US007315623B2

(12) United States Patent
Gierl et al.

(10) Patent No.: US 7,315,623 B2
(45) Date of Patent: Jan. 1, 2008

(54) METHOD FOR SUPRESSING SURROUNDING NOISE IN A HANDS-FREE DEVICE AND HANDS-FREE DEVICE

(75) Inventors: Stefan Gierl, Karlsruhe (DE); Christoph Benz, Ohlsbach (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 177 days.

(21) Appl. No.: 10/497,748

(22) PCT Filed: Dec. 4, 2002

(86) PCT No.: PCT/EP02/13742

§ 371 (c)(1), (2), (4) Date: Feb. 9, 2005

(87) PCT Pub. No.: WO03/049082

PCT Pub. Date: Jun. 12, 2003

(65) Prior Publication Data

US 2005/0152559 A1 Jul. 14, 2005

(30) Foreign Application Priority Data

Dec. 4, 2001 (DE) ................................ 101 59 281

(51) Int. Cl.
*A61F 11/06* (2006.01)

(52) U.S. Cl. .................................................. 381/71.12

(58) Field of Classification Search .... 381/71.1–71.14, 381/93, 83, 94.1–94.9; 455/501; 704/226
See application file for complete search history.

(56) References Cited

U.S. PATENT DOCUMENTS 5,400,409 A * 3/1995 Linhard ....................... 381/92
5,539,859 A * 7/1996 Robbe et al. ............... 704/233

(Continued)

FOREIGN PATENT DOCUMENTS

DE 198 18 608 10/1999

OTHER PUBLICATIONS

Gierl, Stefan. "Geräuschreduktion bei Sprachübertragung mit Hilfe von Mikrofonarraysystemen", Dissertation Universität Karlsruhe, Jul. 1990, pp. 1-129.

(Continued)

*Primary Examiner*—Vivian Chin
*Assistant Examiner*—Lao Lun-See
(74) *Attorney, Agent, or Firm*—O'Shea Getz & Kosakowski, P.C.

(57) ABSTRACT

In order to suppress as much noise as possible in a hands-free device in a motor vehicle, for example, two microphones (M1, M2) are spaced a certain distance apart, the output signals (MS1, MS2) of which are added in an adder (AD) and subtracted in a subtracter (SU). The sum signal (S) of the adder (AD) undergoes a Fourier transform in a first Fourier transformer (F1), and the difference signal (D) of the subtracter (SU) undergoes a Fourier transform in a second Fourier transformer (F2). From the two Fourier transforms R(f) and D(f), a speech pause detector (P) detects speech pauses, during which a third arithmetic unit (R) calculates the transfer function $H_T$ of an adaptive transformation filter (TF). The transfer function of a spectral subtraction filter (SF), at the input of which the Fourier transform R(f) of the sum signal (S) is applied, is generated from the spectral power density $S_{rr}$ of the sum signal (S) and from the interference power density $S_{nn}$ generated by the adaptive transformation filter (TF). The output of the spectral subtraction filter (SF) is connected to the input of an inverse Fourier transformer (IF), at the output of which an audio signal (A) can be picked up in the time domain which is essentially free of ambient noise.

19 Claims, 1 Drawing Sheet

U.S. PATENT DOCUMENTS

| | | | | |
|---|---|---|---|---|
| 5,742,927 | A * | 4/1998 | Crozier et al. | 704/226 |
| 5,943,429 | A * | 8/1999 | Handel | 381/94.2 |
| 6,339,758 | B1 * | 1/2002 | Kanazawa et al. | 704/226 |
| 6,463,408 | B1 * | 10/2002 | Krasny et al. | 704/217 |
| 6,717,991 | B1 * | 4/2004 | Gustafsson et al. | 375/285 |
| 2002/0193130 | A1 * | 12/2002 | Yang et al. | 455/501 |
| 2003/0027600 | A1 * | 2/2003 | Krasny et al. | 455/564 |
| 2003/0040908 | A1 * | 2/2003 | Yang et al. | 704/233 |
| 2003/0086575 | A1 * | 5/2003 | Balan et al. | 381/94.2 |

OTHER PUBLICATIONS

Martinez et al. "Combination of adaptive filtering and spectral subtraction for noise removal", Circuits and Systems, 2001. ISCAS 2001. The 2001 IEEE International Symposium. vol. 2, May 2001, pp. 793-796.

* cited by examiner

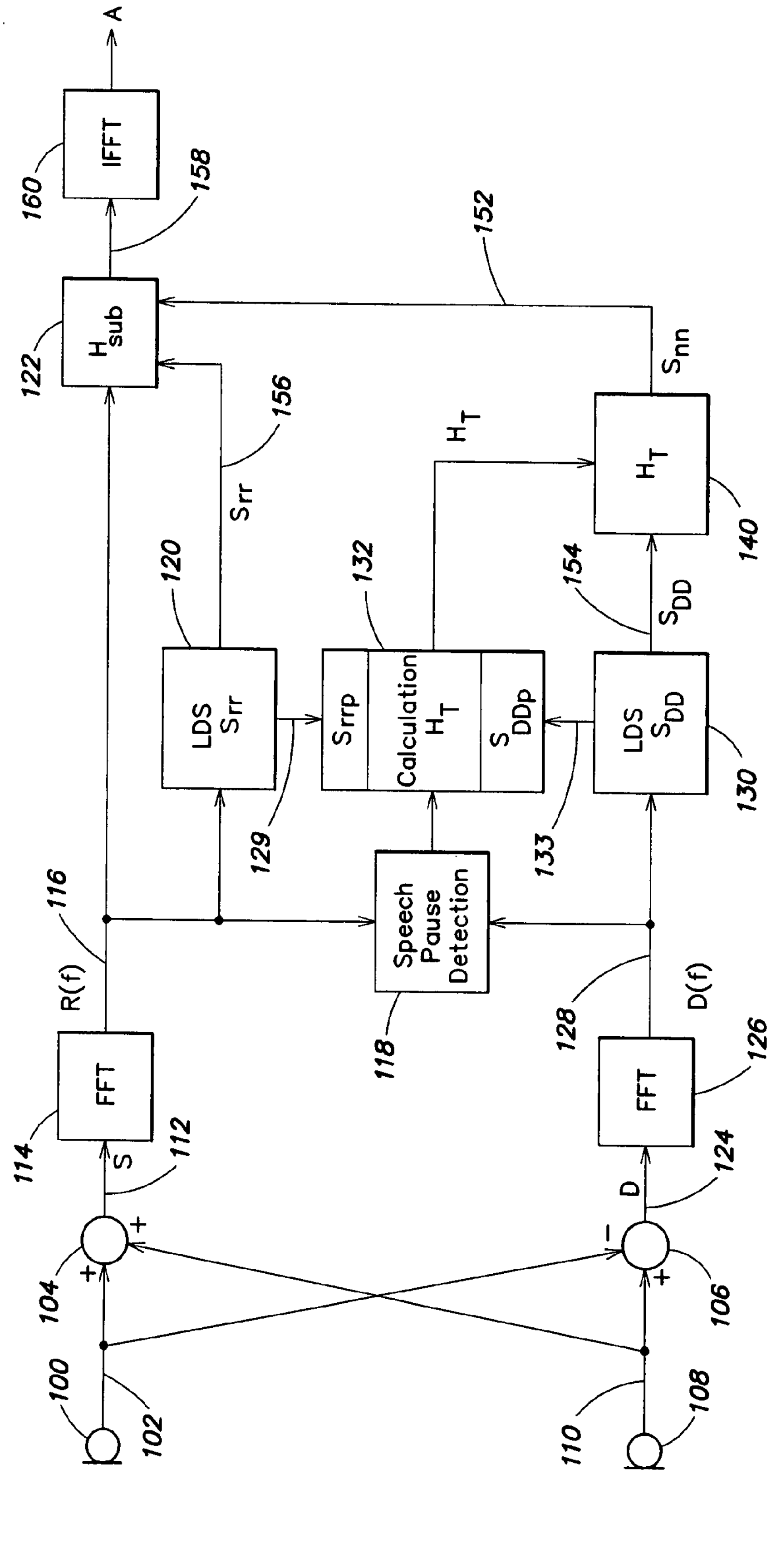
FIG

METHOD FOR SUPRESSING SURROUNDING NOISE IN A HANDS-FREE DEVICE AND HANDS-FREE DEVICE

BACKGROUND OF THE INVENTION

The invention relates to suppressing ambient noise in a hands-free device having two microphones spaced a predetermined distance apart.

Ambient noise represents a significant interference factor for the use of hands-free devices, which interference factor can significantly degrade the intelligibility of speech. Car phones are equipped with hands-free devices to allow the driver to concentrate fully on driving the vehicle and on traffic. However, particularly loud and interfering ambient noise is encountered in a vehicle.

There is a need for a technique of suppressing ambient noise for a hands-free device.

SUMMARY OF THE INVENTION

A hands-free device is equipped with two microphones spaced a predetermined distance apart. The distance selected for the speaker relative to the microphones is smaller than the so-called diffuse-field distance, so that the direct sound components from the speaker at the location of the microphones predominate over the reflective components occurring within the space.

From the microphone signals supplied by the microphones, the sum and difference signal is generated from which the Fourier transform of the sum signal and the Fourier transform of the difference signal are generated.

From these Fourier transforms, the speech pauses are detected, for example, by determining their average short-term power levels. During speech pauses, the short-term power levels of the sum and difference signal are approximately equal, since for uncorrelated signal components it is unimportant whether these are added or subtracted before the calculation of power, whereas, based on the strongly correlated speech component, when speech begins the short-term power within the sum signal rises significantly relative to the short-term power in the difference signal. This rise is easily detected and exploited to reliably detect a speech pause. As a result, a speech pause can be detected with great reliability even in the case of loud ambient noise.

The spectral power density is determined from the Fourier transform of the sum signal and from the Fourier transform of the difference signal, from which the transfer function for an adaptive transformation filter is calculated. By multiplying the power density of the Fourier transform of the difference signal by its transfer function, this adaptive transformation filter generates the interference power density. From the spectral power density of the Fourier transform of the sum signal and from the interference power density generated by the adaptive transformation filter, the transfer function of an analogous adaptive spectral subtraction filter is calculated that filters the Fourier transform of the sum signal and supplies an audio signal essentially free of ambient noise at its output in the frequency domain, which signal is transformed back to the time domain using an inverse Fourier transform. At the output of this inverse Fourier transform, an audio or speech signal essentially free of ambient noise can be picked up in the time domain and then processed further.

These and other objects, features and advantages of the present invention will become more apparent in light of the following detailed description of preferred embodiments thereof, as illustrated in the accompanying drawings.

BRIEF DESCRIPTION OF THE DRAWINGS

The FIGURE is a block diagram illustration of a device for suppressing ambient noise in a hands-free device.

DETAILED DECRIPTION OF THE INVENTION

The output of a first microphone 100 is provided on a line 102 to an adder 104 and a subtracter 106, while a second microphone 108 provides a sensed signal on a line 110 to the adder 104 and the subtracter 106. The adder 104 provides an output on a line 112 to a first Fourier transformer 114, the output of which on a line 116 is input to a speech pause detector 118, to a first arithmetic unit 120 to calculate the spectral power density $S_{rr}$ of the Fourier transform R(f) of the sum signal, and to an adaptive spectral subtraction filter 122.

The subtracter 106 provides a difference signal on line 124 to second Fourier transformer 126, the output of which on a line 128 is connected to the speech pause detector 118 and to a second arithmetic unit 130 to calculate the spectral power density $S_{DD}$ of the Fourier transform D(f) of the difference signal on the line 124. The first arithmetic unit 120 provides an output on a line 129 to a third arithmetic unit 132 to calculate the transfer function of an adaptive transformation filter 140, and to the adaptive spectral subtraction filter 122, the output of which is connected to an inverse Fourier transformer 160. The second arithmetic unit 130 provides a signal on line 133, indicative of the spectral power density $S_{DD}$ , to the third arithmetic unit 132, and to an adaptive transformation filter 140, the output of which is connected to the adaptive spectral subtraction filter 122. The output of the speech pause detector 118 is also connected to the third arithmetic unit 132, that provides an output which is connected to the control input of the adaptive transformation filter 140.

As mentioned above, the two microphones 100 and 108 are seperated a distance which is smaller than the so-called diffuse-field distance. For this reason, the direct sound components of the speaker predominate at the site of the microphone over the reflection components occurring within a closed space, such as the interior of a vehicle.

The short-term power of the Fourier transform R(f) on the line 116 of the sum signal and of the Fourier transform D(f) on the line 128 of the difference signal is determined in the speech pause detector 118. During pauses in speech, the two short-term power levels differ hardly at all since it is unimportant for the uncorrelated speech components whether they are added or subtracted before the power calculation. When speech begins, on the other hand, the short-term power within the sum signal rises significantly relative to the short-term power in the difference signal due to the strongly correlated speech component. This rise thus indicates the end of a speech pause and the beginning of speech.

The first arithmetic unit 120 uses time averaging to calculate the spectral power density $S_{rr}$ of Fourier transform R(f) on the line 116. Similarly, the second arithmetic unit 130 calculates the spectral power density $S_{DD}$ of the Fourier transform D(f) on the line 128. From the power density $S_{rrp}$(f) and the spectral power density $S_{DDp}$(f) during the speech pauses, the third arithmetic unit 132 calculates the transfer function $H_T$(f) of the adaptive transformation filter 140 using the following equation:

$$H_T(f)=S_{rrp}(f)/S_{DDp}(f) \qquad (1)$$

Preferably, an additional time averaging—that is, a smoothing—of the coefficients of the transfer function thus obtained is used to significantly improve the suppression of ambient noise by preventing the occurrence of so-called artifacts, often called "musical tones."

The spectral power density $S_{rr}(f)$ is obtained from the Fourier transform R(f) of the sum signal on the line 116 by time averaging, while in analogous fashion the spectral power density $S_{DD}(f)$ is calculated by time averaging from the Fourier transform D(f) of the difference signal on the line 128.

For example, the spectral power density $S_{rr}$ is calculated using the following equation (2):

$$S_{rr}(f,k)=c*|R(f)|^2+(1-c)*S_{rr}(f,k-1) \quad (2)$$

In analogous fashion, the spectral power density $S_{DD}(f)$ is, for example, calculated using the equation (3):

$$S_{DD}(f,k)=c*|D(f)|^2+(1-c)*S_{DD}(f,k-1) \quad (3)$$

The term c is a constant between 0 and 1 which determines the averaging time period. When c=1, no time averaging takes place; instead the absolute squares of the Fourier transforms R(f) and D(f) are taken as the estimates for the spectral power densities. The calculation of the residual spectral power densities required to implement the method according to the invention is preferably performed in the same manner.

The adaptive transformation filter 140 uses its transfer function $H_T(f)$ to generate the interference power density $S_{nn}$ on line 152 from the spectral power density $S_{DD}(f)$ on the line 154 using the following equation (4):

$$S_{nn}(f)=H_T*S_{DD}(f) \quad (4)$$

Using the interference power density $S_{nn}$ on the line 152 and the spectral power density $S_{rr}$ on the line 156 the transfer function $H_{sub}$ of the spectral subtraction filter 122 is calculated as specified by equation (5):

$$H_{sub}(f)=1-a*S_{nn}(f)/S_{rr}(f) \text{ for } 1-a*S_{nn}(f)/S_{rr}(f)>b$$

$$H_{sub}(f)=b \text{ for } 1-a*S_{nn}(f)/S_{rr}(f)\leq b$$

The parameter a represents the so-called overestimate factor, while b represents the so-called "spectral floor."

The interference components picked up by the microphones 100 and 108, which strike the microphones as diffuse sound waves, can be viewed as virtually uncorrelated for almost the entire frequency range of interest. However, there does exist for low frequencies a certain correlation dependent on the relative spacing of the two microphones, which correlation results in the interference components contained in the reference signal appearing to be high-pass-filtered to a certain extent. In order to prevent a faulty estimation of the low-frequency interference components in the spectral subtraction, a spectral boost of the low-frequency components of the reference signal is performed by the adaptive transformation filter 140.

The method according to the invention and the hands-free device according to the invention, which are particularly suitable for a car phone, are distinguished by excellent speech quality and intelligibility since the estimated value for the interference power density $S_{nn}$ on the line 152 is continuously updated independently of the speech activity. As a result, the transfer function of spectral subtraction filter 122 is also continuously updated, both during speech activity and during speech pauses. As was mentioned above, speech pauses are detected reliably and precisely, this detection being necessary to update the transformation filter 140.

The audio signal at the output on line 158 of the spectral subtraction filter 122, which signal is essentially free of ambient noise, is fed to the inverse Fourier transformer 160 which transforms the audio signal back to the time domain.

Although the present invention has been illustrated and described with respect to several preferred embodiments thereof, various changes, omissions additions to the form and detail thereof, may be made therein, without departing from the spirit and scope of the invention.

What is claimed is:

1. A method of suppressing ambient noise in a hands-free device having two microphones spaced a predetermined distance apart, each of which supplies a microphone signal, comprising:

generating a sum signal and a difference signal of the two microphone signals;

computing a first Fourier transform R(f) of the sum signal (S) and a second Fourier transform of the difference signal;

detecting speech pauses from the first and second Fourier transforms R(f) and D(f);

determining first spectral power density $S_{rr}$ from the first Fourier transform R(f) of the sum signal (S);

determining second spectral power density $S_{DD}$ from the second Fourier transform D(f) of the difference signal (D);

calculating the transfer function $H_T(f)$ for an adaptive transformation filter from the first spectral power density $S_{rr}$ , and from the second spectral power density $S_{DD}$ ;

generating the interference power density $S_{nn}(f)$ by multiplying the second power density $S_{DD}$ by its transfer function $H_T(f)$;

calculating the transfer function $H_{sub}(f)$ of a spectral subtraction filter from the interference power density $S_{nn}(f)$ and from the first spectral power density $S_{rr}$ ;

filtering the first Fourier transform R(f) with the spectral subtraction filter; and transforming the output signal of the spectral subtraction filter back to the time domain.

2. The method of claim 1, where the transfer function $H_T(f)$ of the transformation filter is generated during speech pauses using the equation:

$$H_T(f)=S_{rrp}(f)/S_{DDp}(f).$$

3. The method of claim 2, where the coefficients of the transfer function $H_T(f)$ of the transformation filter are averaged over time.

4. The method of claim 1, where the calculation of the spectral power density $S_{rr}$ from the first Fourier transform R(f), and of the spectral power density $S_{DD}$ from the second Fourier transform D(f), is performed by time averaging.

5. The method of claim 4, where the first spectral power density $S_{rr}$ is calculated using the equation:

$$S_{rr}(f,k)=c*|R(f)|^2+(1-c)*S_{rr}(f,k-1)$$

where k represents the time index, and c is a constant for determining the averaging period.

6. The method of claim 4, where the second spectral power density $S_{DD}$ is calculated using the following equation:

$$S_{DD}(f,k)=c*|D(f)|^2+(1-c)*S_{DD}(f,k-1)$$

where k represents a time index, and c is a constant for determining the averaging period.

7. The method of claim 1, where in order to detect the speech pauses the short-term power of the first Fourier transform R(f) and of the second Fourier transform D(f) is determined, and that a speech pause is detected whenever the two determined short-term power levels lie within a predetermined common tolerance range.

8. The method of claim 1, where the transfer function $H_{sub}(f)$ of the spectral subtraction filter is calculated using the equations:

$$H_{sub}(f)=1-a*S_{nn}(f)/S_{rr}(f) \text{ for } 1-a*S_{nn}(f)/S_{rr}(f)>b$$

$$H_{sub}(f)=b \text{ for } 1-a*S_{nn}(f)/S_{rr}(f)\leqq b$$

where a represents an overestimation factor and b represents a spectral floor.

9. The method of claim 1, where the transit time differences between the two microphone signals are equalized.

10. A hands-free device having two microphones spaced a predetermined distance apart, where the output of the first microphone is connected to the first input of an adder and to the first input of a subtracter;

that the output of the second microphone is connected to the second input of the adder and the second input of the subtracter;

that the output of the adder is connected to the input of a first Fourier transformer, the output of which is connected to the first input of a speech pause detector, to the input of a first arithmetic unit to calculate the spectral power density $S_{rr}$, and to the input of an adaptive spectral subtraction filter;

that the output of the subtracter is connected to the input of a second Fourier transformer, the output of which is connected to the second input of the speech pause detector, and to the input of a second arithmetic unit to calculate the spectral power density $S_{DD}$;

that the outputs of the speech pause detector, first arithmetic unit, and second arithmetic unit are connected to a third arithmetic unit to calculate the transfer function $H_T(f)$ of an adaptive transformation filter;

that the output of the first arithmetic unit is connected to the first control input of the adaptive spectral subtraction filter;

that the output of the third arithmetic unit is connected to the control input of the adaptive transformation filter, the input of which is connected to the output of the second arithmetic unit, and the output of which is connected to the second control input of the adaptive spectral subtraction filter; and that the output of the adaptive spectral subtraction filter is connected to the input of an inverse Fourier transformer, at the output of which an audio signal can be picked up which has been transformed back to the time domain.

11. The hands-free device of claim 10, where the transfer function $H_T(f)$ of the transformation filter is generated during the speech pauses using the following equation:

$$H_T(f)=S_{rrp}(f)/S_{DDp}(f).$$

12. The hands-free device of claim 11, where the coefficients of the transfer function $H_T(f)$ of the transformation filter are averaged over time.

13. The hands-free device of claim 10, where the spectral power density $S_{rr}$ is generated by time averaging from the Fourier transform R(f) of the sum signal, and that the spectral power density $S_{DD}$ is generated by time averaging from the Fourier transform D(f) of the difference signal.

14. The hands-free device of claim 13, where the spectral power density $S_{rr}$ is generated using the equation:

$$S_{rr}(f,k)=c*|R(f)|^2+(1-c)*S_{rr}(f,k-1)$$

where k represents a time index and c is a constant to determine the averaging period.

15. The hands-free device of claim 13, where the spectral power density $S_{DD}$ is calculated using the equation:

$$S_{DD}(f,k)=c*|D(f)|^2+(1-c)*S_{DD}(f,k-1)$$

where k represents a time index, and c is a constant to determine the averaging period.

16. The hands-free device of claim 10, where the transfer function $H_{sub}(f)$ of the spectral function filter is calculated using the following equation:

$$H_{sub}(f)=1-a*S_{nn}(f)/S_{rr}(f) \text{ for } 1-a*S_{nn}(f)/S_{rr}(f)>b$$

$$H_{sub}(f)=b \text{ for } 1-a*S_{nn}(f)/S_{rr}(f)\leqq b$$

where a represents the so-called "overestimate factor" and b represents the "spectral floor.

17. The hands-free device of claim 10, where the transit time differences between the two microphone signals are able to be equalized.

18. A hands-free device that receives a first input signal from a first microphone and a second input signal from a second microphone spaced a predetermined distance from the first microphone, the device comprising:

a summer that sums the first and second input signals to provide a summed signal;

a difference unit that provides a difference signal indicative of the difference between the first and second input signals;

a first time-to-frequency domain transform unit that receives the sum signal and provides a first frequency domain signal indicative thereof;

a second time-to-frequency domain transform unit that receives the difference signal and provides a second frequency domain signal indicative thereof;

a speech pause detector that receives the first and second frequency domain signals and provides a speech pause signal;

a first arithmetic unit that receives the first frequency domain signal and calculates a first spectral power density $S_{rr}$ of the first frequency domain signal;

a second arithmetic unit that receives the second frequency domain signal and calculates a second spectral power density $S_{DD}$ of the second frequency domain signal;

a third arithmetic unit that receives the first and second spectral power density signals and the speech pause signal, and calculates a transfer function $H_T(f)$;

an adaptive transformation filter that receives the transfer function $H_T(f)$ and filters the second spectral power density $S_{DD}$ according to the transfer function $H_T(f)$ to provide an interference power density signal;

an adaptive spectral subtraction filter that receives the first frequency domain signal, first spectral power density $S_{rr}$ and the interference power density signal and filters the first frequency domain signal to provide a filtered signal; and a frequency-to-time domain transform unit that receives the filtered signal and transforms the filtered signal to the time domain to provide a processed signal.

19. A hands-free device that receives a first input signal from a first microphone and a second input signal from a second microphone spaced a predetermined distance from the first microphone, the device comprising:

a summer that sums the first and second input signals to provide a summed signal;

a difference unit that provides a difference signal indicative of the difference between the first and second input signals;

a first time-to-frequency domain transform unit that receives the sum signal and provides a first frequency domain signal indicative thereof;

a second time-to-frequency domain transform unit that receives the difference signal and provides a second frequency domain signal indicative thereof;

a speech pause detector that receives the first and second frequency domain signals and provides a speech pause signal;

a first arithmetic unit that receives the first frequency domain signal and calculates a first spectral power density $S_{r'r'}$ of the first frequency domain signal;

means for calculating a first spectral power density $S_{r'r'}$ of the first frequency domain signal, for calculating a second spectral power density $S_{DD}$ of the second frequency domain signal, and for calculating transfer function $H_T(f)$ based upon the first and second spectral power density signals and the speech pause signal;

a first filter that filters the second spectral power density $S_{DD}$ according to the transfer function $H_T(f)$ to provide an interference power density signal;

a second filter that filters the first frequency domain signal based upon the first spectral power density $S_{r'r'}$ and the interference power density signal, to provide a filtered signal; and a frequency-to-time domain transform unit that receives the filtered signal and transforms the filtered signal to the time domain to provide a processed signal.

* * * * *

UNITED STATES PATENT AND TRADEMARK OFFICE

CERTIFICATE OF CORRECTION

PATENT NO. : 7,315,623 B2
APPLICATION NO. : 10/497748
DATED : January 1, 2008
INVENTOR(S) : Gierl et al.

It is certified that error appears in the above-identified patent and that said Letters Patent is hereby corrected as shown below:

On the Front Page
In the title, delete the current title and insert --SYSTEM FOR SUPPRESSING AMBIENT NOISE IN A HANDS-FREE DEVICE--

Column 2
Line 19, delete "DECRIPTION" and insert --DESCRIPTION--
Line 40, delete "seperated" and insert --separated--
Line 59, before "Fourier" insert --the--
Line 65, before "spectral" insert --the--

Column 4
Line 9, before "additions" insert --and--

Signed and Sealed this

Thirteenth Day of May, 2008

Jon W. Dudas

JON W. DUDAS
*Director of the United States Patent and Trademark Office*

UNITED STATES PATENT AND TRADEMARK OFFICE

CERTIFICATE OF CORRECTION

PATENT NO. : 7,315,623 B2
APPLICATION NO. : 10/497748
DATED : January 1, 2008
INVENTOR(S) : Gierl et al.

It is certified that error appears in the above-identified patent and that said Letters Patent is hereby corrected as shown below:

On the Front Page
In the title, Item [54] and Column 1, lines 1-3 delete the current title and insert
--SYSTEM FOR SUPPRESSING AMBIENT NOISE IN A HANDS-FREE DEVICE--

Column 2
Line 19, delete "DECRIPTION" and insert --DESCRIPTION--
Line 40, delete "seperated" and insert --separated--
Line 59, before "Fourier" insert --the--
Line 65, before "spectral" insert --the--

Column 4
Line 9, before "additions" insert --and--

This certificate supersedes the Certificate of Correction issued May 13, 2008.

Signed and Sealed this

Third Day of June, 2008

Jon W. Dudas

JON W. DUDAS
*Director of the United States Patent and Trademark Office*